United States Patent [19]

Goel

[11] Patent Number: 4,526,722

[45] Date of Patent: Jul. 2, 1985

[54] MANUFACTURE OF DIACYLOXY AROMATIC COMPOUNDS

[75] Inventor: Anil B. Goel, Worthington, Ohio

[73] Assignee: Ashland Oil, Inc., Ashland, Ky.

[21] Appl. No.: 486,150

[22] Filed: Apr. 18, 1983

[51] Int. Cl.$^3$ .......................... C11C 3/02; C07C 67/00
[52] U.S. Cl. .................................. 260/410.5; 560/131
[58] Field of Search ...................... 260/410.5; 560/131

[56] References Cited

U.S. PATENT DOCUMENTS 4,464,303  8/1984  Goel ................................. 260/410.5

Primary Examiner—Anton H. Sutto

Attorney, Agent, or Firm—John F. Jones

[57] ABSTRACT

A process is described for the manufacture of diacyloxy aromatic hydrocarbons by the liquid phase reaction of an aromatic hydrocarbon or a monoacyloxy aromatic hydrocarbon with molecular oxygen in the presence of a carboxylic acid over a catalyst composed of a compound of palladium, a compound of antimony and a compound of at least one member selected from the group consisting of an alkali metal, chromium, zinc, antimony and tin wherein the water formed in the reaction is rapidly and continuously removed from the reaction as it forms.

6 Claims, No Drawings

MANUFACTURE OF DIACYLOXY AROMATIC COMPOUNDS

CROSS-REFERENCE TO RELATED APPLICATIONS

This invention is an improvement over the processes described and claimed in copending U.S. patent applications of Ser. No. 416,809, of Anil B. Goel, filed Sept. 13, 1982, now U.S. Pat. No. 4,464,303, and Ser. No. 441,360, of Anil B. Goel and Peter E. Throckmorton, filed Nov. 15, 1982, U.S. Pat. No. 4,465,633.

BACKGROUND OF THE INVENTION

1. Field of the Invention

The present invention provides a process for preparing aryl diesters from aromatic hydrocarbons such as benzene, naphthalene, anthracene, phenanthrene, fluorene, biphenyl, terphenyls, and the like, which comprises reacting a mixture of the aromatic hydrocarbon, for instance naphthalene, a carboxylic acid, and molecular oxygen in the liquid phase in the presence of a catalyst consisting essentially of palladium or a compound of palladium, a compound of antimony and a compound of at least one member selected from the group consisting of an alkali metal, chromium, zinc, antimony and tin.

2. Description of the Prior Art

The manufacture of phenol by direct oxidation of benzene with oxygen is known. There are, for instance, thermal processes which are performed at very high temperatures in which phenol formed is susceptible to further oxidation so that considerable loss of yield occurs as is disclosed in U.S. Pat. No. 2,223,383. In the presence of catalysts, the oxidation can be carried out at somewhat lower temperatures as in U.S. Pat. No. 3,133,122, but the reactions have been plagued by low conversions and excessive production of unwanted by-products as discussed in U.S. Pat. No. 2,392,875.

It has already been proposed to make phenyl acetate and biphenyl from benzene and acetic acid in the liquid phase in the presence of palladium acetate and without added molecular oxygen by a stoichiometric reaction in *Chem. and Ind.*, Mar. 12, 1966, Page 457.

U.S. Pat. No. 3,542,852 discloses the preparation of hydroxy aromatic compounds by reaction of an aromatic compound and oxygen in the presence of a catalyst composed of iron, a noble metal or a compound of either in the presence of a nitrate ion and a carboxylic acid. More recently, the preparation of phenyl esters and phenols by the reaction of benzene, molecular oxygen and a lower aliphatic carboxylic acid in the presence of a catalyst composed of a Group VIII metal (U.S. Pat. No. 3,642,873) or a compound of such metal (U.S. Pat. No. 3,651,127) have been disclosed. Similarly, variations in this type of reaction have been disclosed in U.S. Pat. Nos. 3,646,111; 3,651,101; 3,772,383; 3,959,352 and 3,959,354. U.S. Pat. No. 3,959,354 concludes that liquid phase reactions of this type because of problems of catalyst elution, etc., are disadvantageous for an industrial process. U.S. Pat. No. 3,772,383 describes a liquid phase reaction using a very complex catalyst system which includes the use of nitric acid and a lower aliphatic carboxylic acid. U.S. Pat. No. 3,644,486 discusses the production of acylation products of condensed aromatic compounds in the liquid phase with oxygen and a saturated carboxylic acid in the presence of a noble metal or compound thereof.

Generally speaking, these prior art processes deal for the most part with vapor phase oxidation reactions, or liquid phase reactions in which all the reactants (except oxygen in some instances) are initially included in the reaction mixtures. Moreover, in general the prior art catalytic processes have produced very low conversions, usually less than 10%, with low selectivity to the desired monophenyl ester, and phenol or phenolic materials are often a primary product of the oxidation reaction. None of the prior art processes show the production of diacyloxy products nor do any of them show the continuous removal of water from the reaction mixture as it forms.

SUMMARY OF THE INVENTION

I have discovered an oxidation process for the transformation of naphthalene, benzene, and similar aromatic hydrocarbons, molecular oxygen and a carboxylic acid to the corresponding aromatic dicarboxylate in high conversions and selectivities to the desired product. The process involves the use of a liquid phase and a catalyst composed of palladium or a compound of palladium with a compound of antimony and at least one compound of a member selected from the group consisting of an alkali metal (such as potassium), chromium, zinc, manganese and tin. I have also discovered that high conversions and high selectivity to the diacyloxy aromatic compounds are continuous removal of water from the reaction mixture as it forms during the entire course of the reaction. If water, which is a by-product of the reaction, is allowed to remain in the reaction mixture it can cause hydrolysis of the diacyloxy aromatic compound to form phenolic materials which in turn can cause deactivation of the catalyst.

The catalysts useful in my process are preferably composed of palladium metal or compounds of palladium and usually a palladium carboxylate in conjunction with an antimony compound and a compound of at least one member selected from the group consisting of an alkali metal (preferably potassium), chromium, zinc, manganese and tin. The catalysts useful in the process of this invention may be used alone or may be supported on a carrier or carriers. Suitable carriers include silica, alumina, carbon, quartz, pumice, diatomaceous earth, and the like and others which are well known in the art.

Carboxylic acids useful in our invention are the monocarboxylic acids which correspond to the formula RCOOH wherein R is a hydrocarbon group having from 1 to 19 carbon atoms. Some carboxylic acid anhydride can be included in the reaction if desired.

Our liquid phase oxidation process produces in the case of naphthalene or alpha-acyloxy naphthalene conversions of 10% or greater with selectivities in the order of 100% to the diacyloxy naphthalene. The diacyloxy products of this process can be readily converted to the dihydroxy aromatic compound by hydrolysis or pyrolysis.

DESCRIPTION OF THE PREFERRED EMBODIMENTS

In a typical reaction in accordance with this invention a mixture of naphthalene, the carboxylic acid and optionally an inert solvent such as n-heptane is contacted in the liquid phase with molecular oxygen and a catalyst at a reaction temperature in the range of from about 100° to 300° C. and preferably at from 140° to 200° C. and at from 1 to 100 and preferably 1 to 10 atmospheres but most preferably at or near atmospheric pressure. The molecular oxygen can be oxygen per se, or any gaseous mixture containing oxygen and other inert gases such as nitrogen, argon, carbon dioxide, etc. For instance, molecular oxygen used in the process of this invention can be in the form of air for convenience.

The catalyst can be a mixture of palladium diacetate, antimony triacetate and at least one member selected from the group consisting of potassium acetate, chromium acetate, zinc acetate, manganese acetate and tin acetate. The molar ratio of Pd:Sb:other metal should be in the range of 1:50:20 to 1:0.1: 0.1 and preferably in the range 1:20:10 to 1:0.2:0.2.

During the process of this invention the water formed is removed continuously as it forms usually by azeotropic distillation with an excess of reactant or with an inert solvent which can be present in the reaction mixture. Inert solvents which can be included in the reaction mixture used in the process of this invention include linear hydrocarbons having the formula $C_nH_{2n+2}$ wherein n is from 4 to 14 such as heptane, pentane, hexane, octanes and the like, cyclic hydrocarbons having the formula $C_nH_{2n}$ wherein n is from 4 to 14, and linear and cyclic aliphatic ethers.

Because essentially no phenolic compounds are produced in the process of this invention, it is believed that catalyst activity is maintained for long periods of time under continued use. The rapid removal of water from the reaction mixture is probably at least partly responsible for the absence of phenolic materials in the reaction product. The presence of phenolic materials in the reaction products of prior art processes is believed to be at least partly reponsible for catalyst fouling, short catalyst life and low conversion obtained.

In the process of this invention the starting material can be either an aromatic hydrocarbon or a monoacyloxy aromatic hydrocarbon. In either case the product will be the diacyloxy aromatic hydrocarbon. When naphthalene is used as the starting material, the product is primarily 1,5-diacyloxy naphthalene, when alpha-acyloxy naphthalene is used as starting material, the product is again primarily 1,5-diacyloxy naphthalene but a shorter reaction time is needed to convert the alpha-acyloxy naphthalene. Similarly, when benzene is used as starting material in the process of this invention the product is a mixture of ortho, para and meta diacyloxy benzene and when monoacyloxy benzene is used as starting material the same diacyloxy benzenes are obtained in a shorter reaction time. Thus, part of this invention relates to a process for the conversion of monoacyloxy aromatic hydrocarbons to diacyloxy aromatic hydrocarbons.

This invention is further illustrated in the following examples.

EXAMPLE I

A reactor equipped with a mechanical stirrer, a thermometer with temperature controller and a Dean-Stark type condenser was charged with 0.349 g (1.5 m mols) of Pd(OAc)$_2$, 0.45 g (1.5 m mol) of Sb(OAc)$_3$, 0.15 g (1.5 m mols) of KOAc, 43 g (300 m mols) of octanoic acid, 10 g (78 m mols) of naphthalene and 10 ml of n-heptane. The Dean-Stark type collector was also filled with n-heptane. The reaction mixture was stirred vigorously and brought to the reaction temperature of 170° C. A continuous flow of oxygen at the rate of 50 cc/min was passed through the reaction mixture during the reaction period of 5 hours. About 1.6 ml of water was collected in the Dean-Stark collector during the reaction. The final reaction mixture was found by GLC analysis to contain 40 m mols of monoacyloxy-naphthalene (97% of alpha-naphthyl ester, 3% beta-naphthyl ester) and 24 m mols of diacyloxy-naphthalene (mainly the 1,5-isomer). The reaction was continued for an additional hour and at the end of this time GLC analysis of the reaction mixture showed essentially 100% conversion of the naphthalene and the formation of 28 m mols of diacyloxy naphthalene. This means that 50 m mols of naphthalene were converted to mono acyloxy naphthalene.

EXAMPLE 2

The procedure of Example 1 was followed except that the catalyst was composed of 3 m mols each of the acetate salts of palladium antimony and chromium and 5 g (18.5 m mols) of alpha-naphthyl octanoate were used in place of naphthalene. The reaction time was 4 hours and analysis of the reaction mixture showed that about 50% of the alpha-naphthyl octanoate was converted to dioctanoxy naphthalene (mainly 1,5-isomer).

EXAMPLE 3

The procedure of Example 1 was followed except that 1.5 m mols of Sn(OAc)$_2$ were used instead of KOAc. The reaction was carried out for about 10 hours and produced 6 m mols of the diacyloxy naphthalene along with 54 m mols of the mono acyloxy naphthalene.

EXAMPLE 4

The procedure of Example 1 was followed using 0.31 g (1.4 m mols) of Pd(OAc)$_2$, 0.42 g (1.4 m mols) of Sb(OAc)$_3$, 0.14 g (1.4 m mols) of KOAc, 82 g (568 m mols) of octanoic acid and 10 g (128 m mols) of benzene. The reaction was carried out at 170° C. for 20 hours. GLC analysis of the reaction mixture showed the formation of 80 m mols of phenyl octanoate and 5 m mols of dioctanoxy benzene. The selectivity of the diacyloxy product was about 75% ortho (catechol precursor) and about 20% meta (resorcinol precurser) and 5% para (hydroquinone precurser).

EXAMPLE 5

The procedure of Example 1 was followed using 0.11 g (0.5 m mol) of Pd(OAc)$_2$, 0.15 g (0.5 m mol) of Sb(OAc)$_3$, 0.12 g (0.5 m mol) of Cr(OAc)$_3$.H$_2$O, 308 m mols of octanoic acid and 5 g (64 m mols) of benzene. The reaction was carried out at 182+2° C. and additional benzene was introduced into the reaction mixture occasionally to maintain a steady reflux. The reaction time was five hours. The final reaction mixture was found by GLC analysis to contain 11% by weight of phenyl octanoate and 2% by weight of phenyl dioctanoate (73% ortho, 21% meta and 6% para). A catalytic turnover number (mols of product produced per mol of catalyst) of about 55 was observed.

EXAMPLE 6

The procedure of Example 1 was followed using 3 m mols of Pd(OAc)$_2$, 3 m mols of Sb(OAc)$_3$, 3 m mols of Cr(OAc)$_2$, 360 m mols of octanoic acid, 45.5 m mols of phenyl octanoate and 10 ml of n heptane. Heptane was also included in the Dean Stark tube. The reaction was conducted at 180+2° C. for 5 hours under a constant flow of oxygen at about 50 cc/min. GLC analysis of the product showed a 23% conversion to phenyl octanoate with 10 m mols of dioctanoxy benzene (74% ortho, 20% meta and 6% para) being formed.

EXAMPLE 7

The procedure of Example 6 was followed using 3 m mols of Mn(OAc)$_2$ instead of the Cr(OAc)$_3$. The reaction was carried out for 6 hours during which 20% of the phenyl octanoate was converted giving 8.5 m mols of dioctanoxy benzene.

I claim:

1. A process for the manufacture of diaryl esters consisting essentially of contacting a reaction mixture of benzene or a monophenyl ester, a carboxylic acid and molecular oxygen in the liquid phase at a temperature in the range of from 100° to 300° C. with a catalyst composed of palladium or a compound of palladium, an antimony compound and a compound of at least one member selected from the group consisting of an alkali metal and tin wherein the molar ratio of Pd:Sb:other metals is in the range of 1:50:20 to 1:0.1:0.1.

2. The process of claim 1 wherein the carboxylic acid has the formula RCOOH wherein R is a hydrocarbon group having from 1 to 19 carbon atoms.

3. The process of claim 2 wherein the palladium compound is a palladium carboxylate.

4. The process of claim 3 wherein the antimony compound is an antimony carboxylate.

5. The process of claim 4 wherein the catalyst is composed of palladium acetate, antimony acetate and potassium acetate and the carboxylic acid is octanoic acid.

6. The process of claim 4 wherein the catalyst is composed of palladium acetate, antimony acetate and tin acetate.

* * * * *